United States Patent [19]

Moore, Jr.

[11] 4,051,124

[45] Sept. 27, 1977

[54] PROCESS FOR PRODUCING AN AZONITRILE WITH IMPROVED COLOR FROM AN AMINONITRILE IN AN AQUEOUS SYSTEM COMPRISING MIXED SURFACE ACTIVE COMPOUNDS

[75] Inventor: Earl Phillip Moore, Jr., Hockessin, Del.

[73] Assignee: E. I. Du Pont de Nemours and Company, Wilmington, Del.

[21] Appl. No.: 686,508

[22] Filed: May 14, 1976

[51] Int. Cl.$^2$ .......................................... C07C 107/02
[52] U.S. Cl. ..................................................... 260/192
[58] Field of Search .......................................... 260/192

[56] References Cited

U.S. PATENT DOCUMENTS

| | | | |
|---|---|---|---|
| 2,713,576 | 7/1955 | De Benneville | 260/192 |
| 3,390,146 | 6/1968 | Nield et al. | 260/192 |
| 3,775,395 | 9/1973 | Koyanagi et al. | 260/192 |
| 3,783,148 | 1/1974 | Fuchs | 260/192 |
| 3,937,696 | 2/1976 | Knowles et al. | 260/192 |

Primary Examiner—Floyd D. Higel

[57] ABSTRACT

A process for the preparation of 2,2'-azobis(isobutyronitrile) of improved color which comprises reacting 2-amino-2-methylpropionitrile with a metal hypochlorite, $M(OCl)_x$ where M is selected from sodium, potassium or calcium and $x$ is the valence of M, in the presence of water and a mixture of a quaternary ammonium surface active compound with either a nonionic or amphoteric surface active compound, said mixture having an HLB of about 8 to about 35 at a temperature of about −10° C to about 30° C and recovering the self-precipitated 2,2'-azobis(isobutyronitrile) from the reaction mixture.

13 Claims, No Drawings

PROCESS FOR PRODUCING AN AZONITRILE WITH IMPROVED COLOR FROM AN AMINONITRILE IN AN AQUEOUS SYSTEM COMPRISING MIXED SURFACE ACTIVE COMPOUNDS

BACKGROUND OF THE INVENTION

1. Field of the Invention

This invention relates to an improved process for the preparation of 2,2'-azobis(isobutyronitrile). More specifically this invention relates to a process for the preparation of 2,2'-azobis(isobutyronitrile) of improved color by reacting an aqueous hypochlorite solution with an aminonitrile in the presence of a surface active compound.

2. Prior Art

The symmetrical azobis(alkanonitriles) and their derivatives have been recognized for over 25 years as useful, highly efficient free-radical polymerization initiators but the slow evolution of feasible and/or economical preparative routes have retarded the commercial development of these unique compounds.

The oldest method for producing aliphatic azonitriles commerically, described by Thiele and Heuser in Ann. 290, 1-43 (1896) is based upon the use of relatively expensive hydrazine and its derivatives as a principal raw material. Castle, U.S. Pat. No. 2,515,628, reacted ketones with sodium cyanide and hydrazine hydrochloride in aqueous medium and the resulting hydrazo compounds were oxidized in water or alcohol to the azos. Robertson, U.S. Pat. No. 2,586,995, prepared the ketazines from ketones and hydrazine hydrate, contacted them with liquid hydrogen cyanide to give hydrazo compounds and oxidized these to the azos. Both of the above procedures gave poor-to-fair yields of azonitriles. A significant process improvement in the hydrazine-based route was made by Koyanagi et al., U.S. Pat. No. 3,775,395, who reacted a ketone, a hydrazine compound and hydrogen cyanide in aqueous medium in the presence of a surface active agent to form the hydrazo compound. Overall yields of azos were excellent.

A second method of producing azonitriles is described by Anderson, U.S. Pat. No. 2,711,405, which involves reacting the cyanohydrin of an aliphatic ketone with ammonia to form an aminonitrile and oxidatively coupling the aminonitrile to form the azo using an alkali metal or alkaline earth metal hypochlorite in aqueous medium. De Benneville, U.S. Pat. No. 2,713,576, claimed essentially the same process with the addition of alkyl hypochlorites and restriction of aminonitriles to those of acetone, methyl ethyl ketone and diethyl ketone. Although the process as disclosed in the Anderson and De Benneville patents is useful for the preparation of azobisisobutyronitrile from the aminonitrile of acetone, the coupling step results in extremely poor yields when applied to aminonitriles of higher molecular weight ketones. A process improvement which enables azonitriles to be prepared from aminonitriles of higher molecular weight ketones in good yields is reported by Fuchs, U.S. Pat. No. 3,783,148. Methanol or ethanol is employed as a reaction solvent in proportion to the amounts of aminonitrile and hypochlorite solution used such that, at the completion of the reaction, the alcohol concentration is at least 70% by volume. The alcohol maintains a homogeneous system throughout the reaction and specifically prevents separation of the intermediate, highly hydrophobic chloramines.

The Fuchs process, however, has its drawbacks. For economic reasons, the alcohol solvent must be recovered; even then, some loss of alcohol occurs due to evaporation, side reactions, etc. The alcohol also interacts with the hypochlorite compound, giving an organic alkyl hypochlorite, which can decompose in a highly exothermic reaction which imposes severe restrictions on the temperature and conditions under which the azonitrile preparation can be carried out. Equipment and manpower requirements to maintain these stringent conditions, the temperature at below $-5°$ C during the simultaneous addition of aminonitrile and hypochlorite to minimize alkyl hypochlorite decomposition, are costly. In addition, the Fuchs process yields product slurries with low solids centent are obtained, because of the alcohol and water requirements to effect this process. This incurs considerable liquid handling and disposal per pound of product with unfavorable labor costs and production limits.

In application Ser. No. 618,761, a process for preparing aliphatic azodinitriles free of the above disadvantages is disclosed. Aliphatic azodinitriles are prepared by reacting a metal hypochlorite with an aminonitrile in water containing a surfactant. The azodinitriles prepared are in the form of an emulsion that is broken with a precipitating agent such as $SO_2$ which also functions as a decolorizer. The product azobisisobutyronitrile possesses a selfbreaking emulsion property but the azobisisobutyronitrile product produced without a precipitating agent possesses an unacceptable color.

SUMMARY OF THE INVENTION

Now it has been found that when 2,2'-azobis(isobutyronitrile) is prepared from 2-amino-2-methyl propionitrile reacted with a metal hypochlorite wherein the metal is selected from sodium, potassium and calcium in the presence of water and a surface active compound, the 2,2'-azobis(isobutyronitrile) produced possesses improved color properties when the surface active compound is a mixture of a quaternary ammonium compound and a compound selected from the groups consisting of a nonionic and amphoteric surface active compound. Accordingly, the process of the present invention comprises reacting 2-amino-2-methylpropionitrile with a metal hypochlorite in an aqueous medium of 5 to 15% by weight initial concentration of said hypochlorite in the presence of 0.25 to 10% by weight (based on the weight of said aminonitrile) of a mixture of a surface active quaternary ammonium salt compound with a compound selected from the group consisting of a nonionic and amphoteric surface active compound, said mixture having an HLB of about 8 to about 35 at a temperature of about $-10°$ C to about 30° C said metal hypochlorite and aminonitrile being present in an equivalent ratio of from 1:1 to 2:1 of hypochlorite to aminonitrile and recovering self-precipitating 2,2'-azobis(isobutyronitrile) of improved color from the reaction mixture.

In the process of the present invention, two molecules of the 2-amino-2-methyl propionitrile are coupled to form the azodinitrile of the present invention. The coupling of the two molecules is accomplished in an aqueous medium with a metal hypochlorite represented by the formula $M(OCl)_x$, wherein M is selected from sodium, potassium and calcium and $x$ is the valence of the M ion, and a surface active compound comprising a mixture of a quaternary ammonium compound with a compound selected from the group consisting of a nonionic and amphoteric surface active compound.

In the process of the invention, the equivalent ratio of hypochlorite to aminonitrile is not critical. However, at equivalent ratios below 1:1 of hypochlorite to aminonitrile the yield is less desirable. At equivalent ratios above 2:1 there is no advantage. Generally, the equivalent ratio of 1:1 to 2:1 will give high yields although the ratio of 1.15:1 to 1.5:1 is preferred because of the especially high yields that result. The equivalent ratio referred to herein is defined as the equivalent of metal hypochlorite per mole of aminonitrile. An equivalent of metal hypochlorite is a mole of the hypochlorite divided by the valence of the metal. An equivalent of aminonitrile is the same as the molar amount of aminonitrile.

The 2-amino-2-methyl propionitrile starting material of the present invention can be obtained from commercial sources or may be prepared by methods well known in the art, for example, by the method described by Anderson in U.S. Pat. No. 2,711,405. A procedure that can be used to obtain the amino compound involves charging the ketone to a platinum-lined pressure vessel and cooling this to dry ice-acetone temperature and then adding 5 to 10 grams of ammonia. Hydrogen cyanide is then introduced in portions in an amount equimolar to that of the keton. The reaction vessel is warmed to room temperature and pressurized to 50 psig with ammonia, heated to 40° C and held at 40° C and 50 psig for 8 hours and finally cooled and the product is discharged from the vessel.

The hypochlorite of the present invention is a metal hypochlorite represented by the formula $M(OCl)_x$ where M is selected from sodium, potassium and calcium and $x$ is the valence of M. For reasons of convenience and economy, sodium hypochlorite is the preferred hypochlorite. Sodium hypochlorite can be prepared by passing chlorine gas in an aqueous sodium hydroxide solution at about 0° C or it can be purchased commercially. Other hypochlorites can be prepared analogously.

The surface active compounds of the present invention affect the surface tension when mixed with water and are not adversely affected in their properties if they react with the hypochlorite, aminonitrile, chloramine intermediate or final product of the present invention.

The use of the mixed surface active compounds of the present invention is a critical feature of this invention. Generally the inclusion of a surfactant as disclosed in U.S. application Ser. No. 618,761, in the process of coupling an aminonitrile to give an azonitrile with hypochlorite enables the reaction quite surprisingly to proceed in strictly aqueous medium. While the function of the surfactant in promoting this coupling reaction is unknown, it may be as a "catalyst" for the reaction of base (e.g., NaOH) with intermediate formed chloramines and/or it may serve as a "solubilizer" for the chloramine and base, or it may perform some other function which enables a reaction to occur.

Surfactants for preparing emulsions are discussed by Paul Becher in "Emulsions, Theory and Practice", ACS Monograph No. 162, 1965. On pages 232–255, Becher discusses the importance of the Hydrophilic-Lipophilic Balance of a surfactant (HLB for short) on its ability to serve as an emulsifying agent in a particular application. The HLB numbers which have been assigned to many surfactants indicate balance in their affiniity for water (hydrophilic) or nonpolar organic liquids (lipophilic). A high HLB number indicates high water solubility and low organic solubility, a low number indicates a high organic solubility and low water solubility.

In the process of this invention, the apparent importance of HLB number of surfactants on their ability to cause the reaction of sodium hypochlorite and aminonitrile was found. Surfactant mixtures with HLB numbers within the range of about 8.0 to about 35.0 generally will result in the preparation of the product of this invention.

The mixed surface active compounds useful in the process of the present invention may have one component of the mixture with an HLB number outside the range described herein as long as the HLB of the mixture is within said range.

The surface active compounds of the present invention are mixtures of a quaternary ammonium surface active compound with a surface active compound selected from nonionic and amphoteric surface active compounds.

Preferred mixture of the surface active compounds of the present invention include nonionic surface active compounds.

Although the presence of the mixed surface active compounds of the present invention is critical, the amount may vary widely. As little as 0.25% by weight of surface active compounds based on the aminonitrile can be used and while the upper limit is not critical, there is no advantage in using more than 10% by weight. For example, at levels above 10% by weight there is no improvement in yield. The preferred range however of 0.3 to 2% by weight of surface active compounds based on the aminonitrile gives the most desirable yield.

The atmospheric pressure system is entirely aqueous, requiring no organic solvent to be present as a promoter or cosolvent with water. The mixed surface active compound is mixed with the water as is the sodium hypochlorite or other metal hypochlorite in the preferred system and the aminonitrile is added with sufficient cooling to handle the heat load. Cooling requirements are less demanding than in the Fuchs process because there is no loss of active halogen through methyl hypochlorite decomposition.

During the reaction period, it is observed that unlike the reaction with other aminonitriles disclosed in U.S. application Ser. No. 618,761, an emulsion of milk-like appearance due to an emulsion of the azodinitrile products does not form with the aminonitrile of this invention. The product of the present invention is entirely a solids suspension and therefore an emulsion breaking or precipitating agent is not required. Thus, for example, the precipitating agents sodium bisulfite or $SO_2$ and hydrochloric or sulfuric acids are not required for the preparation of 2,2'-azobis(isobutyronitrile). When the mixed surface active compounds of the present invention are not used but a surfactant disclosed in U.S. application Ser. No. 618,761 is used, the addition of a precipitating agent results in an improved color quality of the 2,2'azobis(isobutyronitrile). However, in the present invention the product possesses an improved color quality without the addition of said precipitating agents.

The manner in which the sodium hypochlorite and aminonitrile are combined is a matter of choice. The reactants can be added in separate streams to a body of water containing the surface active compound or the aminonitrile can be added to a sodium hypochlorite solution containing the surfactant. This latter method which is preferred is not possible with the Fuchs methanol system where simultaneous addition of reactants into a large volume of methanol is required to minimize the formation of methyl hypochlorite and the heat produced by its decomposition. Furthermore, the Fuchs process requires that a large volume of water be added to precipitate the azo compound. In our preferred system much higher azo solids slurries are possible than with the Fuchs process, enabling higher throughput with time and labor savings providing marked economic benefits. Thus, while product slurries with about 3% solids are obtained with the Fuchs process, the solids content of slurries of the present process is limited only by the upper practical limit of the hypochlorite concentration, which for the preferred sodium hypochlorite is about 15 to 16%. At this upper limit of sodium hypochlorite concentration, a slurry solids content of greater than 10% can be obtained. Actually, however, any concentration of sodium hypochlorite less than about 16% can be used, but 5 to 15% is preferred. With less than 5%, yields of product tend to drop off. However, calcium hypochlorite, which is available as a 100% active material, is diluted to attain the preferred 5 to 15% range. Potassium hypochlorite solutions of the above concentration can also be prepared.

The quaternary ammonium surface active compounds of this invention include various types of nitrogen containing compounds such as fatty alkyl amines and their salts and quaternary ammonium compounds or more specifically tetraalkyl ammonium compounds. The quaternary ammonium surface active compounds of this invention may be also described as having the general formula selected from the group consisting of

$$R-N^+-R'_3 X^-  \quad (1)$$

where R is an alkyl group of 10 to 18 carbon atoms, R' is methyl or ethyl and X is chlorine, bromine or acetate;

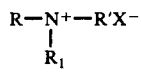
$$R-N^+-R'X^- \atop R_1 \quad (2)$$

where R and $R_1$ are the same or different alkyl groups of 6 to 16 carbon atoms, R' is methyl or ethyl and X is chlorine, bromine or acetate;

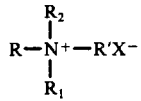
$$\begin{array}{c} R_2 \\ | \\ R-N^+-R'X^- \\ | \\ R_1 \end{array} \quad (3)$$

where R, $R_1$ and $R_2$ are the same or different alkyl groups of 6 to 14 carbon atoms, R' is methyl or ethyl and X is chlorine, bromine and acetate; and

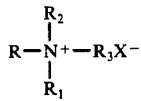
$$\begin{array}{c} R_2 \\ | \\ R-N^+-R_3 X^- \\ | \\ R_1 \end{array} \quad (4)$$

where R, $R_1$, $R_2$ and $R_3$ are the same or different alkyl groups of 6 to 12 carbon atoms and X is chlorine, bromine and acetate.

Tetraalkyl ammonium halides are considered to be the most important type of quaternary ammonium compounds of this invention. The tetraalkyl ammonium chlorides or bromides are preferred. The tetraalkyl ammonium chlorides are considered the most preferred. What is meant by tetraalkyl ammonium in the compounds described herein is that they contain a nitrogen atom to which four separate carbon atoms are attached.

Representative examples of tetraalkyl ammonium surface active compounds of the present invention include:

| Compound | Trade Name | Manufacturer |
|---|---|---|
| Dioctyldimethylammonium chloride | Bordac LF | Lonza, Inc. |
| Hexadecyltrimethyl-ammonium bromide | Retarder LAN | Du Pont Co. |
| Tallowtrimethyl-ammonium chloride | Arquad T-50 | Armak Co. |
| Decyltrimethylammonium chloride | | |
| Dodecyltrimethyl-ammonium chloride | Arquad 12-50 | Armak Co. |
| Tetradecyltrimethyl-ammonium chloride | | |
| Hexadecyltrimethyl-ammonium chloride | Arquad 16-50 | Armak Co. |
| Octadecyltrimethyl-ammonium chloride | Arquad 18-50 | Armak Co. |
| Trioctylmethylammonium chloride | Aliquat 336 | General Mills Chemical Co. |

For economic reasons the alkyl ammonium chloride compounds are preferred.

The mixed surface active compounds in the present process, preferably include nonionic types.

Representative examples of nonionic surfactants include complex polyoxyalkylene glycols, polyoxyalkylene fatty acid esters, polyoxyalkylene alkyl aryl ethers, polyoxyalkylene fatty alcohol ethers, polyoxyethylene sorbitol fatty acid esters, amine oxides, polyoxyethylene sorbitan fatty acid esters, alkylene oxide-ethylene diamine condensation compounds and others, disclosed in McCutcheons' "Detergents & Emulsifiers", North American Edition, 1974 Annual, published by McCutcheon's Division, Allured Publishing Corporation, Ridgewood, New Jersey.

Representative examples of the above indicated nonionic surfactants are shown in the tables that follow with their trade names and manufactures:

TABLE I

| Complex Polyoxyalkylene Glycols | |
|---|---|
| Pluronic L-64 (BASF Wyandotte Co.) | Condensate of ethylene oxide with a hydrophobic base formed by condensing propylene oxide with propylene glycol |
| Pluronic 17R8 (BASF Wyandotte Co.) | Condensate of propylene oxide with a hydrophilic base formed by condensing ethylene oxide with ethylene glycol |

TABLE II

| Polyoxylakylene Fatty Acid Esters | |
|---|---|
| Emcol H-35A (Witco Chemical Corp.) | Polyethylene glycol (400) monostearate |
| Hodag 60-L (Hodag Chemical Corp.) | Polyoxyethylene glycol (600) monolaurate |
| Lipal 15T (PVO International) | Polyoxyethylene tallate |

TABLE II

| Polyoxyalkylene Alkylaryl Ethers | |
|---|---|
| Igepal CO-630 (GAF Corp.) | Nonylphenoxypoly(ethyleneoxy) ethanol |
| T-DET DD-9 (Thompson-Hayward Chem. Co.) | Dodecylphenol-ethylene oxide adduct |
| Poly-Tergent B-350 (Olin Corp.) | Nonylphenoxy polyethoxyethanol |

TABLE IV

| Polyoxyalkylene Fatty Alcohol Ethers | |
|---|---|
| Ameroxol OE-20 (Amerchol Corp.) | Ethoxylated oleyl alcohol |
| Arosurf 66-E20 (Ashland Chem. Co.) | Polyoxyalkylated isostearyl alcohol |
| Brij 35 (ICI America, Inc.) | Polyoxyethylene (23) lauryl ether |
| Merpol HCS (Du Pont Co.) | Polyoxyethylene lauryl ether |

TABLE V

| Polyoxyethylene Sorbitol Fatty Acid Esters | |
|---|---|
| Atlas G-1471 (ICI America, Inc.) | Polyoxyethylene sorbitol lanolin deriv. |
| Atlas G-1086 (ICI America, Inc.) | Polyoxyethylene sorbitol oleate |

TABLE VI

| Amine Oxides | |
|---|---|
| Ammonyx CO | Cetyl dimethyl amine oxide |
| Ammonyx SO | Stearyl dimethyl amine oxide |
| Conco XA-L (Continental Co.) | Lauryl dimethyl amine oxide |

TABLE VII

| Polyoxyethylene Sorbitan Fatty Acid Esters | |
|---|---|
| Drawmulse POE-SMO (PVO International) | Ethoxylated sorbitan monooleate |
| Hallco-CPH-375-N (C. P. Hall Co.) | Polyoxyethylene (20) sorbitan monolaurate |
| Tween 60 (ICI America, Inc.) | Polyoxyethylene (20) sorbitan monostearate |

Table VIII

| Alkylene Oxide-Ethylene Diamine Condensation Compounds* | |
|---|---|
| Tetronic 504, 704, 904, etc. (BASF Wyandotte Corp.) | Compounds formed by addition of propylene oxide to ethylenediamine, followed by the addition of ethylene oxide |

*Also considered as cationic surfactants in acid medium.

Nonionic surfactants in addition to those falling in the above classes or compounds that are within the scope of the present invention include lecithin and its derivatives such as soya lecithin, silicone glycol copolymers, fluorochemical compounds, complex polyesters of polyoxyethylene glycol phosphate esters, polymers such as poly(vinyl alcohol) resins, glycol esters such as diethylene glycol oleate, propylene glycol monolaurate and sorbitan monopalmitate.

Representative examples of amphoteric surface active compounds include those with a dual character such as cationic-anionic such as:

| | |
|---|---|
| Velvetex BCW (Textilana Corp.) | Coco dimethylammonium carboxylic acid betaine. |
| Product DDN (E. I. du Pont de Nemours & Co.) | N-lauryl betaine. |

The mixed surface active compounds of this invention are mixtures of a quaternary ammonium compound with one or more of the above nonionic, or amphoteric surface active compounds.

The rate at which the aminonitrile can be added to the hypochlorite and surface active compound mixture depends on the size of the batch and the capabilities of the cooling equipment. However, the rate can be much more rapid than in prior art processes utilizing methanol. The cooling requirements of the present process are markedly lower than those of the process involving methanol. The methanol process muct avoid the highly exothermic decomposition of methyl hypochlorite. Therefore, the process, of the present invention can be operated at higher temperatures than those possible in the methanol process and thus permit an economic benefit over the methanol process because of the much lesser need for cooling equipment and associated systems. The preferred temperature of the present process is 5° C to 15° C but temperature may vary beyond our preferred temperature range in the process of the present invention. Desirable yields can be obtained at temperatures as low as −10° C and as high as 30° C. The process of the present invention can be conducted at temperatures below −10° C but at lower temperatures the danger of freezing of the aqueous mixture becomes greater and reaction times become longer. The use of antifreeze compounds may permit operation of the present process at temperatures lower than −10° C without freezing. The process of the present invention can also be carried out at temperatures above 30° C but at higher temperatures the risk of side reactions, azo decomposition and lower product yields becomes a serious consideration. Thus, the process of the present invention may be conducted at a temperature that is above the freezong point of the reaction mixture and below the decomposition temperature of the azodinitrile compounds.

The time required to complete the reaction of the present invention is dependent on temperature. At the preferred temperature range of 5° to 15° C, the reaction takes about 30 minutes. At a temperature of −5° C, the reaction will take about one hour. At 30° C, the reaction can be complete in 10 minutes. The time required for the reaction for a specific product at a specific temperature and batch size can readily be determined.

The yields attained by the process of the present invention, while substantially greater than the yields attained by the process described in Fuch's U.S. Pat. No. 3,783,148 involving methanol, are equivalent to that obtained in U.S. application Ser. No. 618,761.

Generally, the pressure in the process of the present invention is atmospheric.

The invention is further illustrated by the examples that follow, wherein all percentages are by weight unless otherwise indicated. APHA color determinations were by procedure 118 "Color" page 160 (1971) of Standard Methods for Examination of Water and Waste Water.

EXAMPLE 1

Sixty grams of 2-amino-2-methyl propionitrile (81% purity) were added over a period of 20 minutes to a stirred mixture of 495 g 10% sodium hypochlorite solution and 0.25 g hexadecyltrimethyl ammonium chloride cooled at 50° C. The reaction mixture was stirred for 30 minutes at 10° C, filtered under vacuum in a Buchner funnel and the cake was washed with 950 ml water and pressed dry. Complete drying was conducted at 45° C in a forced air oven.

There was obtained 44.5 g of azobisisobutyronitrile (a 93.8% yield). A 2 g sample was dissolved in dimethylformamide to give 100 ml solution. Fifty ml of this solution were placed in a colorimetric glass tube and APHA color was determined against APHA color standards in water. The APHA value was 50, unacceptably high for application of this initiator in polymerizations by most polymer producers.

EXAMPLE 2

The procedure of Example 1 was repeated except that a mixture of surface active compounds comprised of 0.15 g hexadecyltrimethyl ammonium chloride and 0.58 g of a 60% solution of a polyoxyethylene lauryl ether (Merpol HCS, Du Pont Co.) was used. The proportion of surface active compounds on a 100% solids basis was 30:70.

44.3 g 2,2'-azobis(isobutyronitrile) (93.4% yield) was obtained. A solution of the product in dimethylformamide gave an APHA color of 10, below the specification of 15 acceptable to the polymer industry.

EXAMPLES 3 TO 7

In the following examples, 0.15 g of the following quaternary ammonium salts are used in place of the hexadecyltrimethyl ammonium chloride of Example 2 following the procedure of Example 2.

| Example | Compound | APHA No. | Grams Product | % Yield |
|---|---|---|---|---|
| 3 | Dodecyltrimethyl ammonium chloride | 9 | 43.0 | 90.6 |
| 4 | Decyltrimethyl ammonium chloride | 7 | 42.8 | 90.2 |
| 5 | Octadecyltrimethyl ammonium chloride | 10 | 44.0 | 92.7 |
| 6 | Dioctyldimethyl ammonium chloride | 12 | 45.4 | 95.7 |
| 7 | Trioctylmethyl ammonium chloride | 10 | 45.2 | 95.3 |

EXAMPLES 8 TO 13

In the following examples, the following surface active compounds are used in place of merpol HCS in Example 2 using the procedure of Example 2. The proportion of surfactants in each example, on a 100% solids basis, is 30:70.

| Example | Compound | APHA No. | Grams Product | % Yield |
|---|---|---|---|---|
| 8 | Lauryl dimethylamine oxide (30% solv., Conco XA-L, Continental Chemical Co.), 1.16 g (nonionic) | 11 | 44.1 | 93.0 |
| 9 | N-lauryl Betaine (25% solu., Product DDN, Du Pont Co.), 1.4 g (amphoteric) | 13 | 44.1 | 93.0 |
| 10 | Propylene oxide-Ethylene oxide condensation product (BASF Wyandotte Co., Pluronic L-64), 0.35 g (nonionic) | 11 | 43.0 | 90.6 |
| 11 | Polyoxyethylene Monolaurate (Hodag 60-L, Hodag Corp.), 0.35 g (nonionic) | 9 | 43.8 | 92.3 |
| 12 | Nonylphenol ethylene oxide adduct (T-DET N-14, Thompson Hayward Co.), 0.35 g (nonionic) | 12 | 43.2 | 91.1 |
| 13 | Polyoxyethylene sorbitan monolaurate (Tween 20, Rohm & Haas Co.), 0.35 g (nonionic) | 13 | 42.9 | 90.4 |

EXAMPLES 14 TO 17

In the following examples, Merpol HCS and hexadecyltrimethyl ammonium chloride were mixed in different proportion following the procedure of Example 2.

| Example | Hexadecyltrimethyl/Merpol HCS (100% solids basis) | | APHA No. | Grams Product | % Yield |
|---|---|---|---|---|---|
| 14 | 20:80 | 1 g mix. in Example 2 recipe | 9 | 44.1 | 93.0 |
| 15 | 40:60 | 0.5 g mix. | 11 | 44.3 | 93.4 |
| 16 | 50:50 | 0.5 g mix. | 14 | 45.0 | 94.9 |
| 17 | 60:40 | 0.4 g mix. | 15 | 43.9 | 92.5 |

A higher proportion can be used but is not advisable since the acceptable APHA 15 may be exceeded.

The eudiometric technique for determining purity of the azodinitriles of this invention is readily available in E. I. du pont de Nemours and Company, Standard Method No. V 38.029(B) (Industrial Chemicals Dept.) published 1/17/69, entitled *Vazo® Vinyl Polymerization Catalyst-Determination of Assay-Pyrolytic, Eudiometric Method.*

The 2,2'-azobis(isobutyronitrile) of the present invention is useful as an initiator in free radical polymerization reactions.

While certain representative embodiments and details have been shown for the purpose of illustrating the invention, it will be apparent to those skilled in this art that various changes and modifications may be made therein without departing from the spirit or scope of the invention.

What is claimed is:
1. A process for the preparation of 2,2'-azobis(isobutyronitrile) of improved color comprising reacting 2-amino-2-methylpropionitrile with a metal hypochlorite, $M(OCl)_x$ where M is selected from sodium, potassium or calcium and $x$ is the valence of M, in an aqueous medium having an initial concentration of 5 to 15% by weight metal hypochlorite in the presence of 0.25 to 10% by weight, based on the weight of said aminonitrile, of a mixture of a quaternary ammonium surface active compound with a compound selected from a nonionic and amphoteric surface active compound said mixture having and HLB of about 8 to about 35 at a temperature of about $-10°$ C to about $30°$ C said metal hypochlorite and aminonitrile being present in an equivalent ratio of from 1:1 to 2:1 of hypochlorite to aminonitrile and recovering the self-precipitated 2,2'azobis(isobutyronitrile) from the reaction mixture without the use of a precipitating agent.

2. The process of claim 1 wherein the equivalent ratio of hypochlorite to aminonitrile is from 1.15:1 to 1.15:1.

3. The process of claim 1 wherein the metal, M, is sodium.

4. The process of claim 1 wherein the surface active compound is 0.3 to 2.0% by weight of the aminonitrile.

5. The process of claim 1 wherein the temperature is from 5° to 15° C.

6. The process of claim 1 wherein the surface active compound is a mixture of a quaternary ammonium surface active compound and an amphoteric surface active compound.

7. The process of claim 1 wherein quaternary ammonium surface active compound is a tetraalkylammonium halide.

8. The process of claim 1 wherein the quaternary ammonium surface active compound is an alkyltrimethylammonium chloride or bromide.

9. The process of claim 1 wherein the quaternary ammonium surface active compound is hexadecyltrimethylammonium chloride.

10. The process of claim 1 wherein the quaternary ammonium surface active compound is dioctyldimethylammonium chloride.

11. The process of claim 1 conducted in the presence of a mixture of a quaternary ammonium surface active compound and a nonionic surface active compound.

12. The process of claim 11 wherein the nonionic surface active compound is selected from the group consisting of a complex polyoxyalkylene glycol, polyoxyalkylene fatty acid esters, polyoxyalkylene alkyl aryl ethers, polyoxyalkylene fatty alcohol ethers and polyoxyethylene sorbitan fatty acid esters.

13. The process of claim 12 wherein the polyoxyalkylene fatty alcohol ether is a polyoxyethylene lauryl ether.

* * * * *

UNITED STATES PATENT OFFICE
CERTIFICATE OF CORRECTION

PATENT NO. : 4,051,124
DATED : SEPTEMBER 27, 1977
INVENTOR(S) : EARL PHILLIP MOORE, JR.

It is certified that error appears in the above-identified patent and that said Letters Patent are hereby corrected as shown below:

Column 4, line 7, "number" should be -- numbers --.

Column 7, line 1, "TABLE II" should be -- TABLE III --.

Column 8, line 16, "muct" should be -- must --.

Column 8, line 40, "freezong" should be -- freezing --.

Column 10, Table, Example 8, line 2, "(30% solv.," should be -- (30% solu., --.

Column 11, line 19, "1.15:1", second occurrence, should be -- 1.5:1 --.

Signed and Sealed this

Thirtieth Day of May 1978

[SEAL]

Attest:

RUTH C. MASON
Attesting Officer

LUTRELLE F. PARKER
Acting Commissioner of Patents and Trademarks